US006933293B2

(12) United States Patent
Ruigt et al.

(10) Patent No.: US 6,933,293 B2
(45) Date of Patent: Aug. 23, 2005

(54) USE OF MIRTAZAPINE FOR THE TREATMENT OF SLEEP DISORDERS

(75) Inventors: Gerardus Stephanus Franciscus Ruigt, Oss (NL); Frans Van den Berg, Vianen (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/203,232

(22) PCT Filed: Feb. 6, 2001

(86) PCT No.: PCT/EP01/01221

§ 371 (c)(1),
(2), (4) Date: Aug. 7, 2002

(87) PCT Pub. No.: WO01/58453

PCT Pub. Date: Aug. 16, 2001

(65) Prior Publication Data

US 2003/0022888 A1 Jan. 30, 2003

(30) Foreign Application Priority Data

Feb. 11, 2000 (EP) .............................................. 00200499

(51) Int. Cl.[7] .............................................. A61K 31/55
(52) U.S. Cl. .................................................. 514/214.02
(58) Field of Search .................................... 514/214.02

(56) References Cited

U.S. PATENT DOCUMENTS 6,303,595 B1   10/2001   Andrews

FOREIGN PATENT DOCUMENTS

| EP | 0 813 873 A | 12/1997 |
| WO | 99 25356 A | 5/1999 |

OTHER PUBLICATIONS

Roth et al, Clinical Cornerstone, 5(3) 2003, 5–12, abstract.*
Roth et al, Sleep, 18(4) 1995, 246–251, abstract.*
Czeisler, Charles A. et al.: "Disorders of Sleep and Circadian Rhythms" Harrisons Principals of Internal Medicine, 14th ed. McGraw Hill (1998) pp150–151.
Riemann, D. et al., "The Guideline for 'Non–Restorative Sleep': Relevance for the Diagnosis and Therapy of Insomnia", Somnologie, 7: 66–76, 2003.
Ruigt, G.S.F., et al: "High and Low Doses of Mirtazapine Have Different Effects On Sleep"; 6th World Congress Biological Psychiatry NICE Jun. 22–27, 1997.
Sennef, C. et al: Effects of mirtazapine, amitriptyline and their combination on sleep in healthy volunteers measured by an ambulatory digital recording system (VITAPORT II®); 21st CINP Glasgow, Jul. 12–16, 1998.
Ruigt, G.S.F. et al: "Computer–Based Prediction of Psychotropic Drug Classes Based on a Discriminant Analysis of Drug Effects on Rat Sleep"; Neuropsychobiology 1993: 28: 138–153.

Ruigt, G.S.F.: "Sleep–Wake Research in The Netherlands"; Dutch society for sleep–wake research; vol. 6 (1995), pp 109–114.
Fawcett et al: "Review of the results from clinical studies on the efficacy, safety and tolerability of mirtazapine for the treatment of patients with major depression"; Journal of Affective Disorders, 51 (1998) pp 267–285.
Fink et al: "Pharmaco–EEG Study of 6–Azamianserin (Org 3770): Dissociation of EEG and Pharmacologic Predictors of Antidepressant Activity"; Psychopharmacology, (1982) 78: 44–48.
Bremner, James D., M.D.: "A Double–Blind Comparison or Org 3770, Amitriptyline, and Placebo in Major Depression"; Journal of Clinical Psychiatry 56:11, Nov. 1995, pp 519–525.
Database Drugnl 'Online! "Organon's Mirtazapine Still Available for Licensing in the USA", Database accession No. 92:603, Jul. 13, 1992.
E. Vester et al.: "Anxiolytic and sleep improving effects of mirtazapine in everyday clinical practice" European Neuropsychopharmacology, vol. 7, No. Suppl. 2, 1997, p. S175.
Ramaekers J G et al: "Effects of nocturnal doses of mirtazapine and mianserin on sleep and on daytime psychomotor and driving performance in young, healthy volunteers." Human Psychopharmacology, vol. 13, No. Supple. 2, Nov. 1998, pp. S87–S97.
Ruigt G S et al: "Effect of the Antidepressant Org–3770 on Human Sleep" European Journal of Clinical Pharmacology, vol. 38, No. 6, 1990, pp. 551–554.
Westenberg Herman G M: "Pharmacology of antidepressants: Selectivity of multiplicity?" Journal of Clinical Psychiatry, vol. 60, no, Suppl. 17, 1999, pp. 4–8.
Winokur Andrew et al: "Acute effects of mirtazapine on sleep continuity and sleep architecture in depressed patients: A pilot study." Biological Psychiatry, vol. 48, No. 1, Jul. 1, 2000, pp. 75–78.
Thase Michael E: "Antidepressant treatment of the depressed patient with insomnia." Journal of Clinical Psychiatry, vol. 60, No. Suppl. 17, 1999, pp. 28–31.
Sitsen J M A et al: "Mirtazapine, a novel antidepressant, in the treatment of anxiety symptoms: Results from a placebo–controlled trial." Drug Investigation, vol. 8, No. 6, 1994, pp. 339–334.

* cited by examiner

Primary Examiner—Rebecca Cook
(74) Attorney, Agent, or Firm—Mark W. Milstead

(57) ABSTRACT

The invention relates to the use of mirtazapine for the preparation of a medicine for a new method of treatment of a sleep disorder in a subject, which treatment comprises the administration of mirtazapine with a unit treatment dose comprising between 0.1 and 5 mg mirtazapine and relates to a patient pack for the treatment of sleep disorders.

10 Claims, No Drawings

USE OF MIRTAZAPINE FOR THE TREATMENT OF SLEEP DISORDERS

FIELD OF THE INVENTION

The invention relates to the use of mirtazapine for the preparation of a medicine for a new method of treatment of a sleep disorder in a subject.

BACKGROUND OF THE INVENTION

Sleep difficulties are a major motivation for use of drugs. The most often selected drugs are those interacting with the GABA neurotransmitter-receptor system in the brain, the so-called minor tranquillisers, of which the group of benzodiazepine drugs is the classic example. Disadvantages of currently available hypnotics are the potential for adverse reactions, remaining lesser quality of sleep, hangover effects, dependency potential, withdrawal effects and undesirable effects on cognitive functioning. The quality of sleep can not only be derived from the effect of sleep, for example whether the sleep has been refreshing and has a positive effect on daytime drowsiness/alertness the morning after, but also from objective EEG determined characteristics, describing sleep stages and architecture.

The discovery of different types of benzodiazepine receptors are exploited to open new avenues for pharmacotherapy of insomnia (for review see C. K. Kirkwood; Management of insomnia; J Am Pharmaceut. Ass. Vol 39 pp 688–696; 1999). Other mechanisms for inducing sleep are also explored. The opiate-like drugs, the barbiturates and anti-histamines are drug classes which have been used several decades ago as sleep inducers, but their use became obliterated due to undesirable side effects and/or lesser efficacy. Such drugs are still in use for other disorders whereby the main effects would be side effects when used for the treatment of sleep disorders. Specifically, drugs, antagonising histamine receptors are sedative and sleep inducing but are not used regularly anymore for the treatment of sleep disorders in view of lower selectivity, lower potency and lower safety in comparison to benzodiazepines and their modern successors.

Mirtazapine is known as an anti-depressant. It is active for that purpose at daily doses of 15–45 mg per person. It is well-known that the dose is crucial for effective therapy, in particular for the treatment of depression. Mirtazapine is reported to have some initial sedative effects and because of this its effects on sleep have been investigated. It is reported that in the dose range of 5–30 mg per person per day improvement of transient, or situational insomnia is found, whereby the dose of 15 mg was reported to be preferable over 5 mg (Sørensen et al. Acta Psychiatr. Scand. 71: 339–346; 1985). Also Winokur (Biological Psychiatry 1998; 45(8S): p 106S) investigates 15 and 30 mg mirtazapine in depressed patients with prominent sleep related complaints and recommends further investigation of these doses for treatment of sleep disorders.

BRIEF SUMMARY OF THE INVENTION

It has now been found that mirtazapine can be used for the preparation of a medicine for the treatment of a sleep disorder in a subject, which treatment comprises the administration of mirtazapine with a unit treatment dose comprising more than 0.1 and less than 5 mg mirtazapine, which in other words is a unit treatment dose (within the range) between 0.1 and 5 mg mirtazapine.

In general this amounts for an average human person to a treatment dose in the range between 0.005 and 0.07 mg/kg.

In contrast to the expectations, the favourable results which make the compound available as a valid alternative for known drugs of choice for the treatment of sleep disorders were obtained with treatment doses below the dose range studied and recommended by Sørensen et al. and Winokur (cited above). At least for individual patients mirtazapine in the above indicated dose range can be a better choice than a choice of one of the known sleep improving drugs in view of a better quality of sleep after treatment.

DETAILED DESCRIPTION OF THE INVENTION

The amounts of mirtazapine defined in this description refer to the amount of free base of mirtazapine. Mirtazapine contains a centre of chirality and can exist as stereoisomers. The present invention includes the aforementioned stereoisomers within its scope and each of the individual (R) and (S) enantiomer and their salts, substantially free, i.e. associated with less than 5%, preferably less than 2%, in particular less than 1% of the other enantiomer and mixtures of such enantiomers in any proportions including racemic mixtures containing substantially equal amounts of the two enantiomers.

The subject amenable for a treatment made available by this invention can be an animal or a human person. This invention is preferably to be applied for a mammal and more preferably for a human person. Men and women often respond differently to drug treatment and suffer differently in nature, frequency and severity from sleep disorders. Also, there are differences in treatment methods for persons with sleep problems among different age groups. The elderly, adolescents or postmenopausal age groups have different needs for treatment. Certain aspects of sleep quality improvement are more important for different age groups or gender or different sleep disturbances. Such differential factors are to be taken into account in selecting the treatment of this invention and in selecting the exact dose of mirtazapine for the treatment. The very exact dose and regimen of mirtazapine administration will necessarily depend on the needs of the individual subject to whom it is being administered in the form of a medicament and on the nature or needs of the sleep disorder and the judgement of the medical practitioner. In general, parenteral administration requires lower dosages than other methods of administration which are more dependent upon absorption. However, the daily dosages are between 0.005 and 0.07 mg/kg body weight of the recipient. The recipient is the subject receiving the dose of mirtazapine for treatment of a sleep disorder.

There are several types of sleep disorders in man, of which primary insomnia is the most common one and preferably selected to be treated with a low dose of mirtazapine according to this invention. Other sleep disorders are for example transient sleep disorders and secondary sleep disorders. The sleep disorders can be diagnosed according to the criteria and methods outlined in the Diagnostic and Statistical Manual of Mental Disorders 4th edition (DSM IV) published by the American Psychiatric Association, Washington, D.C. (1994).

While it is possible to administer mirtazapine, or a pharmaceutical acceptable acid addition salt or solvate thereof, alone it is preferable to present it as a pharmaceutical composition adapted for the treatment of sleep disorders, comprising the mirtazapine, or a pharmaceutically acceptable acid addition salt or solvate thereof, mixed with one or more pharmaceutically acceptable auxiliaries. The medicament comprising mirtazapine may be administered enterally (e.g. orally, rectal nasal or topically) or parenterally (e.g. via intramuscular, subcutaneous, intravenous or intraperitoneal injections).

A unit treatment dose (=a dosing unit) is an amount of mirtazapine in a pharmaceutical presentation form for administration to a subject at a particular point in time. A daily treatment dose can be administered in one or more dosage units suitable for example for the oral, the rectal, the sublingual or the nasal route or through the skin (for example, transdermal patches, or in the form of a cream).

The invention further includes a patient pack for treatment of sleep disorders comprising dose units in combination with packaging material suitable for said dose units, whereby the dose units comprise pharmaceutical auxiliaries and mirtazapine in an amount between 0.1 and 5 mg and optionally, said packaging material is including means to help a recipient using the dose units most suitably for the treatment of a sleep disorder. Such means to help a recipient using the dose units most suitably for the treatment as described before herein are, for example, instructions for the use of the composition. In such a patient pack the intended use of a formulation comprising mirtazapine for the treatment of sleep disorders can be inferred by instructions, facilities, provisions, adaptations and/or other means to help using the formulation most suitably for the treatment. Such measures make a patient pack specifically suitable for and adapted for use for treatment of a sleep disorder.

For making means of dosing, such as pills, tablets, suppositories, (micro-)capsules, powders, emulsions, creams, ointments, implants, a patch, a gel, and any other preparation for sustained release, sprays, injection preparations in the form of a solution or suspension, suitable auxiliaries such as carriers, fillers, binders, lubricants, dispersants, emulsifiers, stabilisers, surfactants, antioxidants, colorants, preservatives and the like can be used e.g. as described in the standard reference, Gennaro et al., Remington's Pharmaceutical Sciences, (18th ed., Mack Publishing Company, 1990, see especially Part 8: Pharmaceutical Preparations and Their Manufacture). In general any pharmaceutically acceptable auxiliary which does not interfere with the function of the active compounds is suitable and can be used.

Suitable fillers or carriers with which the compositions can be administered include agar, alcohol, fats, lactose, starch, cellulose derivatives, polysaccharides, polyvinylpyrrolidone, silica, sterile saline and the like, or mixtures thereof used in suitable amounts.

Binders are agents used to impart cohesive properties to a pharmaceutical composition resulting in minimal loss from the pharmaceutical composition during production and handling. Binders are for example cellulose, starches, polyvinylpyrrolidone, and the like.

A suitable lubricant with which the active agent of the invention can be administered is, for example, magnesium stearate.

Surfactants are agents facilitating the contact and migration of compounds in different physical environments such as hydrophilic and hydrophobic environments. Many surfactants are known in the art of making pharmaceutical compositions as for example described in chapter 19 of Remington's Pharmaceutical Sciences (18th edition Editor A. R. Gennaro; Mack Publishing Comp; Easton, Pa.). Surfactants that can be used during the process of preparing the pharmaceutical formulation are, for example, polyethylene glycol (PEG), and the like.

Mirtazapine may be prepared using the method described in U.S. Pat. No. 4,062,848 which is incorporated herein by reference.

The following example is an illustration of the use of mirtazapine according to the invention.

EXAMPLE

Mirtazapine is formulated in dosing units containing 0.5 mg, 1.5 mg and 4.5 mg mirtazapine.

The dosing units containing 0.5 mg (as tablets) have the composition as indicated in table 1:

TABLE 1

| Tablet excipients | Per tablet in mg | Per batch in gram |
|---|---|---|
| Mirtazapine | 0.5 | 7.7 |
| Cornstarch | 6.5 | 100.0 |
| Hydroxypropylcellulose | 1.3 | 20.0 |
| Magnesium stearate | 0.4875 | 7.5 |
| Aerosil | 0.975 | 15.0 |
| Lactose 200 M | to 65 mg | to 1000 gram |

For preparation of tablets a 1000 g granulate batch with the composition indicated in table 1 was prepared by pre-mixing the complete amount of mirtazapine (base) with 100 gram of lactose 200 M in a 1 liter glass container for 10 minutes on a Turbula mixer at 22 rotations per minute (rpm). The mixture is sieved through a 150 $\mu$m sieve before and after which a further 20 g of lactose 200 M is added. Granulation was performed in a high shear mixer granulator with the rest of the lactose, corn starch and hydroxypropylcellulose. The granulate was dried in a tray vacuum cabinet, classified with a conical screen mill and mixed with aerosil and magnesium stearate. The 65 mg tablets were compressed with a diameter of 5 mm and a radius of convexity of 7.5 mm. Tablets with 1.5 and 4.5 mg mirtazapine were prepared similarly whereby the quantity of lactose was adapted in order to compensate for the increased quantity of mirtazapine.

Dosing units containing, 1.5 mg and 4.5 mg mirtazapine were prepared analogously with compensatory reduction of the amount of lactose 200 Mesh.

Effects of low dose mirtazapine on sleep in primary insomniac patients: a parallel double blind comparison with placebo and temazepam.

The study is a multi-centre study with participation of centres in several different countries in Europe.

Patients with primary insomnia are selected with diagnosis criteria according to DSM IV. Furthermore, patients should have 2 out of the following three objective characteristics: patients with sleep latency $\geq 30$ min, number of awakenings $\geq 3$ per night, total sleep time $\leq 6,5$ out of 8 hours.

Major exclusion criteria are: secondary insomnia, sleep apnoea syndrome, non-related serious illness or drug abuse.

The study design is parallel, double blind, placebo and active controlled. Patients obtain treatment for 14 days with once daily administration of either 0.5 mg mirtazapine, 1.5 mg mirtazapine, 4.5 mg mirtazapine, 20 mg temazepam or placebo. Observations, assessments and measurements are recorded starting with one placebo treatment week (washout) before the start of the treatment and ending with one placebo treatment week after the treatment to assess rebound/withdrawal.

Assessment methods are poly-somnography (PSG) recordings for the nights of day −2, −1, 1, 13, 14, 15, whereby night −1 is defined to be the night immediately before the first day of the treatment. Subjective ratings with rating scales for sleep and daytime functions (Leeds sleep evaluation questionnaire, MOS sleep rating scale, clinical global impression scale, Bastani mood rating scale, Lader Bond mood rating scale, profile of mood states) are performed with evening and morning questionnaires throughout the study period. Psychometric assessments are performed on the mornings of day 1, 2 and day 15, whereby day 1 is defined to be the first day on which drug or placebo is administered in the evening. Blood is drawn on the mornings of day 1 and day 15 and on the evening of day 15 and assessments are made with recording of vital signs and physical examination and laboratory determinations. The improvement of the quality, including efficacy of sleep and the safety, adverse effects and occurrence of rebound/withdrawal effects of the treatment with drugs is observed in the changes before and after treatment of the various parameters measured with the indicated methods. Specifically the PSG assessments and subjective and objective assessment of sleep and performance the morning after, reveal information on sleep parameters, such as the functional EEG characteristics, the time falling asleep, total sleep time, the frequency and duration of night time awakenings, the time of early morning awakening, fragmentation of sleep, the sensitivity for disruptive stimuli, the feelings of refreshment, restlessness or tiredness after awakening, the sense of balance and co-ordination upon getting up, the sleep hygiene during day time (such as the occurrence of day time naps), the state of performance during daytime reflected in feeling tired, trouble in staying awake during the day, performance in cognitive tests such as simple reaction time, digit vigilance task, choice reaction time, rapid visual information processing, tracking, numeric working memory, word recognition, and daytime feelings of depressed mood, anxiety, confusion, anger, irritability and hangover effects. The Lader Bond mood rating scale provides daytime assessments separately along the dimensions alert/drowsy, calm/excited, strong/feeble, muzzy/clear-headed, well-co-ordinated/clumsy, lethargic/energetic, contented/discontented, troubled/tranquil, mentally slow/quick witted, tense/relaxed, attentive/dreamy, incompetent/proficient, happy/sad, antagonistic/amicable, interested/bored, withdrawn/gregarious, worried/carefree, depressed/elated and self-centered/outward-going. The Bastani visual analogue scale provides daytime assessments separately of the feelings sleepy, nauseated, dizzy, calm, active, anxious, irritable, depressed, good overall, restless, strange, aroused and mellow.

What is claimed is:

1. A method of treatment of primary insomnia in a subject, comprising:
   administering an effective amount of mirtazapine to said subject, wherein the range of the amount is more than 0.1 to less than 5 mg mirtazapine or a pharmaceutically acceptable salt thereof.

2. The method of treatment according to claim 1, wherein mirtazapine is the S enantiomer.

3. A method of treatment of transient sleep disorder in a subject, comprising:
   administering an effective amount of more than 0.1 mg to about 4.5 mg of mirtazapine or a pharmaceutically acceptable salt thereof.

4. The method of treatment according to claim 3, wherein mirtazapine is the S enantiomer.

5. The method of treatment according to claim 1, wherein the range of the amount is more than 0.1 to about 4.5 mg mirtazapine.

6. The method of treatment according to claim 5, wherein the range of the amount is about 0.5 to about 4.5 mg mirtazapine.

7. The method of treatment according to claim 3, wherein the range of the amount is more than 0.5 to about 4.5 mg mirtazapine.

8. A method of treatment of secondary insomnia in a subject, comprising:
   administering an effective amount of more than 0.1 mg to about 4.5 mg of mirtazapine or a pharmaceutically acceptable salt thereof.

9. The method of treatment according to claim 8, wherein mirtazapine is the S enantiomer.

10. The method of treatment according to claim 8, wherein the range of the amount is about 0.5 to about 4.5 mg mirtazapine.

* * * * *